United States Patent [19]

Penning et al.

[11] Patent Number: 5,439,943
[45] Date of Patent: Aug. 8, 1995

[54] NON-STEROID AND NON-PROSTANOID INHIBITORS OF STEROID AND PROSTAGLANDIN TRANSFORMING ENZYMES

[75] Inventors: Trevor M. Penning, Aldan, Pa.; Joseph W. Ricigliano, Piscataway, N.J.

[73] Assignee: Trustees of the University of Pennsylvania, Philadelphia, Pa.

[21] Appl. No.: 336,833

[22] Filed: Nov. 9, 1994

Related U.S. Application Data

[60] Division of Ser. No. 114,737, Aug. 30, 1993, which is a division of Ser. No. 756,505, Sep. 9, 1991, Pat. No. 5,258,296, which is a continuation-in-part of Ser. No. 539,371, Jun. 18, 1990, Pat. No. 5,118,621, which is a continuation of Ser. No. 187,832, Apr. 29, 1988, abandoned.

[51] Int. Cl.⁶ .................. A01N 35/00; A61K 31/11
[52] U.S. Cl. .................. 514/705; 435/184; 435/190
[58] Field of Search .............. 514/705; 435/184, 190

[56] References Cited

U.S. PATENT DOCUMENTS

5,118,621  6/1992  Penning et al. .................. 435/184
5,258,296  11/1993  Penning et al. .................. 435/184

OTHER PUBLICATIONS

Penning et al. (1984) Biochem. J. 222, 601–611.
Penning et al. (1983) Proc. Natl. Acad. Sci., U.S.A. 80, 4504–4508.
Penning et al. (1987) Biochem. Biophys. Res. Comm. 142(2), 646–652.
MacInnes et al., Allylic Inhibitors of Alcohol Dehydrogenase, Journal of the Chemical Society Perkin Transaction 1, 1981, 1103–1108.
Covey et al., Biochemistry 1986, 25, 7288.
Ricigliano et al. Biochem. J. 1989, 262, 139.
Lawate and Covey, J. Med. Chem. 1990, 33, 2319–2321.

*Primary Examiner*—Werren B. Lone
*Attorney, Agent, or Firm*—Woodcock Washburn Kurtz Mackiewicz & Norris

[57] ABSTRACT

Compounds such as 1-(4'-nitrophenyl)-2-propen-1-ol are disclosed which are non-steroidal mechanism-based inactivators of rat liver 3α-hydroxysteroid dehydrogenase. The corresponding ketones are time dependent inactivators of cyclooxygenase (PGH$_2$-synthase).

18 Claims, 5 Drawing Sheets

NON-STEROID AND NON-PROSTANOID INHIBITORS OF STEROID AND PROSTAGLANDIN TRANSFORMING ENZYMES

GOVERNMENT SUPPORT

The government has rights in this invention pursuant to NIH Grant GM 33464, awarded by the Department of Health and Human Services.

RELATED APPLICATIONS

This is a division of application Ser. No. 08/114,737, filed on Aug. 30, 1993, which in turn is a Divisional application of Ser. No. 756,505, filed Sep. 9, 1991, U.S. Pat. No. 5,258,296, issued on Nov. 2, 1993, which in turn is a continuation-in-part of Ser. No. 539,371, filed Jun. 18, 1990 U.S. Pat. No. 5,118,621 issued on Jun. 2, 1992, which is a continuation of Ser. No. 07/187,832 filed on Apr. 29, 1988, abandoned.

FIELD OF THE INVENTION

This invention relates to non-steroidal and non-prostanoid compounds which function as mechanism-based inhibitors for 3α-hydroxysteroid dehydrogenase, hydroxyprostanglandin dehydrogenases and prostaglandin F synthase. The compounds are also irreversible inhibitors for cyclooxygenase.

BACKGROUND OF THE INVENTION

Hydroxysteroid dehydrogenases (HSD's) are a family of enzymes which play a pivotal role in the regulation of steroid hormone action. These enzymes catalyze the interconversion of secondary alcohols to ketones in a positional and stereospecific manner on the steroid nucleus and side chain. They require nicotinamide dinucleotide (phosphate), NAD(P)+, as cofactor. For example, 3α-hydroxysteroid dehydrogenase, (EC 1.1.1.50; 3α-HSD) catalyzes the reduction of 5α-dihydrotestosterone (a potent androgenic steroid hormone) to 5α-androstan-3α,17β-diol (a weak androgen). In this reaction, a 3-ketosteroid is converted to a 3α-hydroxysteroid and, as a result, the potency of the steroid hormone is decreased by five orders of magnitude. Other HSD's carry out reactions of similar importance in the regulation of estrogen, progestin and glucocorticoid action. As a family, HSD's represent target enzymes for drug development.

Research groups headed by Dr. Cecil H. Robinson (Johns Hopkins University) and by Dr. Douglas F. Covey (Washington University School of Medicine) have concentrated on the development of steroidal suicide substrates for HSD's. [BBRC, 1981, 101;2, 495–501; Steroids, 1982, 40;1, 109–119; Steroids, 1979, 34;2, 199–206; Biochemistry, 1986, 25;23, 7295–7300]. Suicide substrates are one class of mechanism-based inhibitors which mimic the normal substrate and are transformed by the enzyme's catalytic mechanism to highly reactive alkylating agents which then inactivate the enzyme by forming a covalent bond at the active site. In this manner, the enzyme catalyzes its own destruction. These compounds have the potential to be highly selective since they are innocuous by themselves until they are transformed by the target enzyme.

Based on the known functions of 3α-HSD, suicide substrates for this enzyme may have a therapeutic use in potentiating the action of androgens and could be used as an adjuvant in androgen replacement therapy. Such therapy is routinely used in the treatment of hypogonadism of pituitary and testicular origin. Androgens are also essential for the maintenance of male fertility. They can be used as anabolic steroids and can act as anti-estrogens.

3α-HSD and several other hydroxysteroid dehydrogenases have been reported to catalyze the oxido-reduction of non-steroidal substrates. Examples include 3β-HSD from *Pseudomonas testosteroni* which reduces cyclohexanone as well as bicyclic and tricyclic ketones [Prog. in Hormone Res., 1967, 23, 349–373], 3α-HSD and 17β-HSD from rat and mouse liver, respectively, which oxidize 1,2-trans-dihydroxy-3,5-cyclo-hexadiene [Biochem. J., 1984, 222;3, 601–611; J. Biol. Chem., 1983, 258;12, 7252–7255], and rat liver 3α-HSD which reduces aromatic ketones and quinones [Biochem. J., 1984, 222;3, 601–611]. These observations suggest that suicide substrates based on non-steroids could provide an alternative rational approach to inhibitor design.

In the present invention, monocyclic-aromatic allylic and acetylenic alcohols are shown to be highly selective inhibitors of 3α-HSD. The non-steroidal nature of these compounds, coupled with the fact they are less expensive and more readily synthesized, indicate that they offer distinct advantages over their steroidal counterparts. This approach may be generally applicable for the development of suicide substrates for other hydroxysteroid dehydrogenases.

Certain suicide substrates of this invention based on monocyclic-aromatic allylic and acetylenic alcohols are transformed by 3α-HSD to monocyclic-aromatic vinyl and acetylenic ketones. These ketones have the unusual property of alkylating the pyridine nucleotide binding site of 3α-HSD. Therefore monocyclic-aromatic vinyl and acetylenic ketones may represent a general class of affinity ligands for pyridine nucleotide binding sites.

A number of additional properties have been assigned to the purified 3α-HSD of rat liver cytosol which suggest that suicide substrates for this enzyme may have broader applications. First, the enzyme can function as a hydroxyprostaglandin dehydrogenase and will catalyze the conversion of PGF$_2$α (a non-inflammatory prostaglandin) to PGE$_2$ (a pro-inflammatory prostaglandin) [BBRC, 1987, 148;2, 646–652]. Second, deduction of the amino acid sequence of the enzyme from its cDNA indicates that 3α-HSD has close sequence homology with prostaglandin F synthase (PGF-synthase) [J. Biol. Chem, 1991, 266;14, 8820–8825]. PGF-synthase catalyses the conversion of PGH$_2$ (an unstable endoperoxy-hydroxyprostaglandin) to the primary prostaglandins which mediate symptoms of inflammation. Third, 3α-HSD is potently inhibited in a competitive fashion by all the major classes of non-steroidal anti-inflammatory drugs (NSAID's) in rank-order of their therapeutic potency. This inhibition occurs at concentrations that are beneath the peak plasma concentrations observed in man [PNAS, 1983, 80;14, 4504–4508]. Fourth, the anti-inflammatory drug-sensitive 3α-HSD is widely distributed in rat tissues. It is found in high levels in tissues which play a role in the metabolism of prostaglandins, in, for example, the lung, heart, seminal vesicle and spleen. [Biochem. Pharm., 1985, 34;6, 831–835]. Collectively, these data suggest that 3α-HSD may be an alternative target for anti-inflammatory drugs.

Because 3α-HSD displays these additional properties, the suicide substrates based on monocyclic-aromatic allylic and acetylenic alcohols of this invention should inactivate hydroxyprostaglandin dehydrogenases and prostaglandin F synthase in a mechanism based manner.

While the monocyclic aromatic allylic and acetylenic alcohols display high selectivity for 3α-HSD, their selectivity can be further enhanced by coupling them to appropriate functionalities to imitate NSAIDs. Once these coupled compounds are oxidized by 3α-HSD to the corresponding ketones they have the capacity to alkylate the NSAID binding site in preference to the NAD(P)+ binding site of 3α-HSD.

The monocyclic-aromatic and coupled ketones of this invention can cause time dependent inactivation of prostaglandin-H synthase (EC 1.14.99.1, PGH-synthase, cyclooxygenase). Cyclooxygenase converts arachidonic acid to prostaglandins which mediate many physiological and pathophysiological processes including inflammation. Cyclooxygenase is a bifunctional enzyme, catalyzing both the oxygenation of arachidonic acid to the hydroperoxy endoperoxide prostaglandin G$_2$ and the reduction of prostaglandin G$_2$ to the hydroxy endoperoxide prostaglandin H$_2$. Cyclooxygenase is the target for a variety of non-steroidal anti-inflammatory drugs. For example, aspirin is Known to inhibit the oxygenase activity of cyclooxygenase by acetylating a single internal serine located within the polypeptide chain.

This invention covers monocyclic-aromatic allylic and acetylenic alcohols, appropriately coupled compounds which imitate NSAIDS, and all enzyme-generated products which mediate enzyme inactivation.

Based upon the known functions of 3α-HSD, hydroxyprostaglandin dehydrogenases, and prostaglandin synthases (PGF synthase and PGH synthase), inhibitors for these enzymes may have a number of broad uses: (1) they may potentiate androgen action and act as adjuvants in androgen therapy; (2) they may represent suicide substrates of hydroxyprostaglandin dehydrogenases and prostaglandin F synthase; (3) they may act as time dependent inactivators of cyclooxygenase; and (4) they may represent a new class of anti-inflammatory drugs.

SUMMARY OF THE INVENTION

Tests by the inventors indicate that 1-(4′-nitrophenyl)-2-propen-1-ol (I) and 1-(4′-nitrophenyl)-2-propyn-1-ol (II) are highly selective mechanism-based inactivators of the enzyme 3α-HSD.

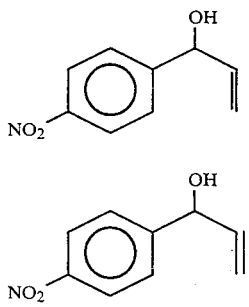

They are oxidized by the enzyme to the corresponding α,β-unsaturated ketones, 1-(4′-nitrophenyl)-2-propen-1-one (III) and 1-(4′-nitrophenyl)-2-propyn-1-one (IV).

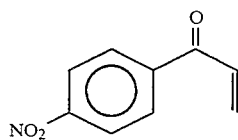

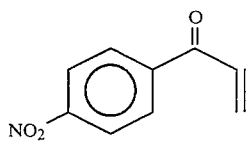

These ketones subsequently inactivate the enzyme by a Michael addition, as shown in Scheme 1 for 1-(4′-nitrophenyl)-2-propen-1-ol, wherein X=any nucleophilic amino acid residue on the enzyme, ENZ.

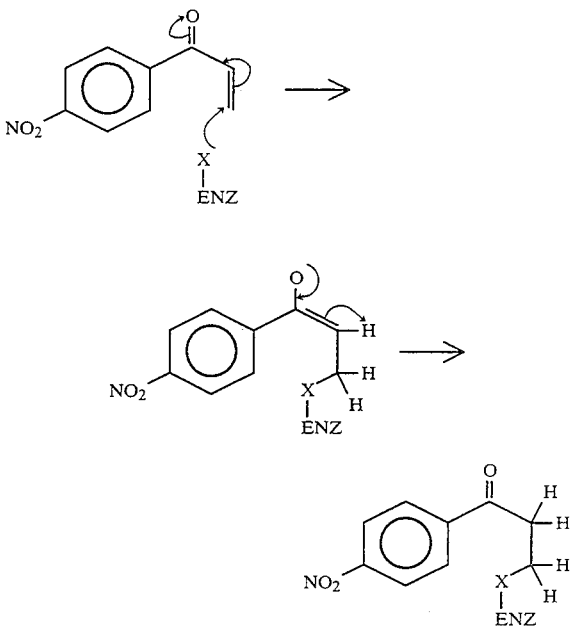

Scheme 1

The ketones, (III) and (IV), are stoichiometric inactivators of 3α-HSD and can be used to titrate the purified enzyme. Current evidence indicates that the pyridine nucleotide binding domain is labeled by the enzyme-generated ketones in preference to the steroid binding site.

By converting the α,β-unsaturated alcohols to analogs that imitate NSAID's, the resulting compounds have the potential to act as NSAID based suicide substrates of 3α-HSD. Exemplary inactivation mechanisms involving N-phenyl-anthranilic acids (V), 1-methyl-pyrrole acetic acids (VI) or aryl propionic acids (VII) are provided in Scheme 2. The enzyme-generated ketones would be expected to alkylate the anti-inflammatory drug binding site 3α-HSD.

Tests by the inventors indicate that 1-(4′-nitrophenyl)-2-propen-1-one (III) and 1-(4′-nitrophenyl-2-propyn-1-one (IV) also irreversibly inactivate prostaglandin synthases in a time dependent manner.

Based on the finding that ketones (iii) and (iv) inactivate cyclooxygenase, α,β-unsaturated alcohols that imitate NSAIDs have the potential to act as pro-drugs. Upon oxidative metabolism to a α,β-unsaturated ketones, the activated compounds could alkylate the anti-inflammatory drug binding site of cyclooxygenase.

Scheme 2

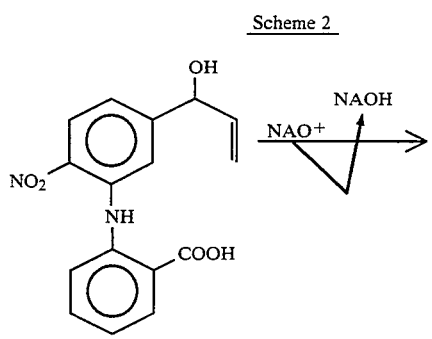

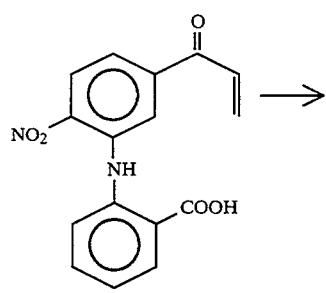

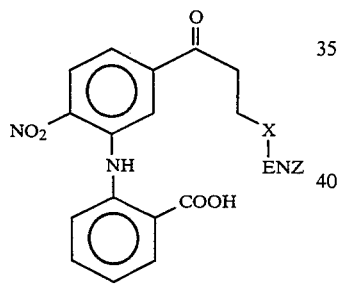

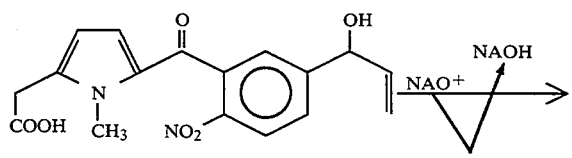

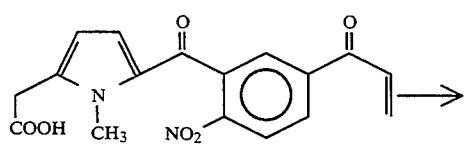

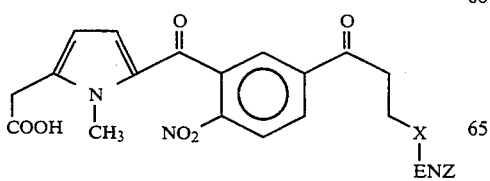

-continued
Scheme 2

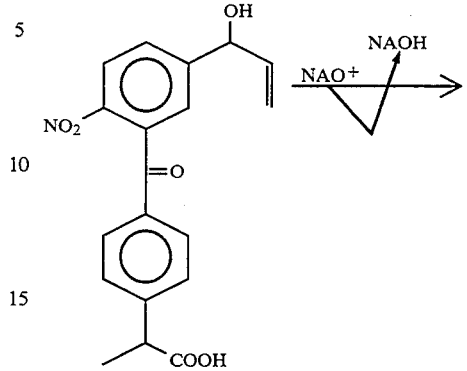

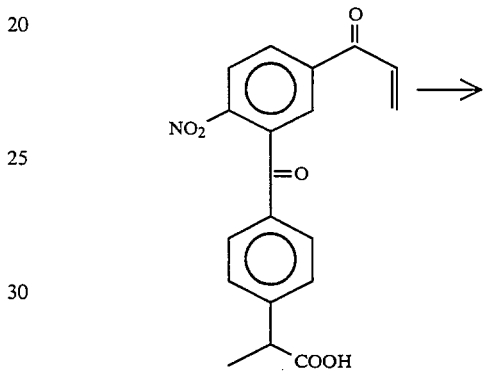

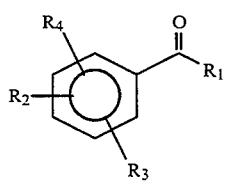

This invention therefore relates to a method of inactivating an enzyme selected from hydroxysteroid dehydrogenases, hydroxyprostaglandin dehydrogenases, and prostaglandin synthases such as PGF-synthase and PGH-synthase, comprising contacting said enzyme or tissue suspected to contain said enzyme with a compound of the formula:

(i)

-continued

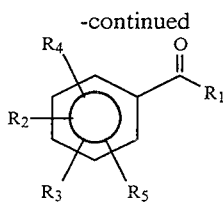
(ii)

where
- $R_1$ is selected from the groups consisting of $CH=CH_2$, $CH=CH-OMe$, $CH=CH-OEt$, $C\equiv CH$, $C\equiv C-OMe$, and $C\equiv C-OEt$;
- $R_2$ is selected from the groups consisting of $NO_2$, Z, $CH_2Z$, $CHZ_2$, $CZ_3$, COOH, $NH_2$ and OH;
- $R_3$ and $R_4$ are independently selected from the groups consisting of H, $NO_2$, Z, $CH_2Z$, $CHZ_2$, $CZ_3$, COOH, $NH_2$ and OH;
- $R_5$ is selected from the groups consisting of:

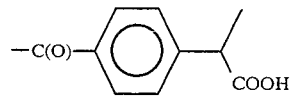

and

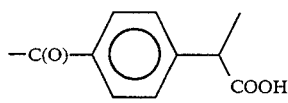

and Z is a halogen atom.

This invention further relates to a method of inactivating an enzyme selected from hydroxysteroid dehydrogenases, hydroxyprostaglandin dehydrogenases, and prostaglandin synthases such as PGF-synthase, comprising contacting said enzyme or tissue suspected to contain said enzyme with a compound of the formula:

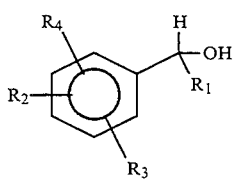
(iii)

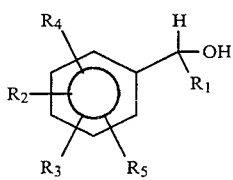
(iv)

where
- $R_1$ is selected from the groups consisting of $CH=CH_2$, $CH=CH-OMe$, $CH=CH-OEt$, $C\equiv CH$, $C\equiv C-OMe$, and $C\equiv C-OEt$;
- $R_2$ is selected from the groups consisting of $NO_2$, Z, $CH_2Z$, $CHZ_2$, $CZ_3$, COOH, $NH_2$ and OH;
- $R_3$ and $R_4$ are independently selected from the groups consisting of H, $NO_2$, Z, $CH_2Z$, $CHZ_2$, $CZ_3$, COOH, $NH_2$ and OH;
- $R_5$ is selected from the groups consisting of

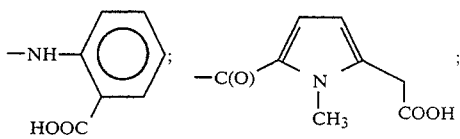

and

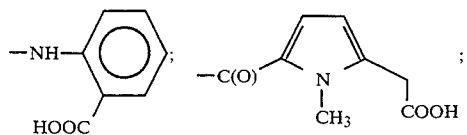

and Z is a halogen atom,
under conditions which allow said enzyme or another moiety to catalyze the oxidation of said compound to the corresponding ketone.

Still further, this invention relates to novel compounds which may be used in the above-mentioned methods. These compounds have the formulas:

(v)

(vi)

where
- A is $-C(O)-$ or $-CH(OH)-$;
- $R_1$ is selected from the groups consisting of $CH=CH_2$, $CH=CH-OMe$, $CH=CH-OEt$, $C\equiv CH$, $C\equiv C-OMe$, and $C\equiv C-OEt$;
- $R_2$ is selected from the groups consisting of $NO_2$, Z, $CH_2Z$, $CHZ_2$, $CZ_3$, COOH, $NH_2$ and OH;
- $R_3$ and $R_4$ are independently selected from the groups consisting of H, $NO_2$, Z, $CH_2Z$, $CHZ_2$, $CZ_3$, COOH, $NH_2$ and OH;
- $R_5$ is selected from the groups consisting of:

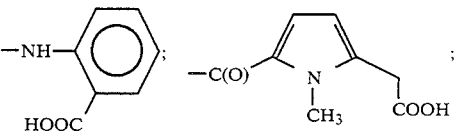

and

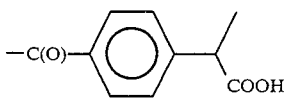

and Z is a halogen atom,
provided that, for compounds of formula (v), when $R_2=NO_2$ and $R_3$ and $R_4=H$, then $A=-CH(OH)-$ and $R_1$ is other than $C\equiv CH$.

Still further, this invention relates to pharmaceutical compositions comprising one of the compounds of formulas (i), (ii), (iii) and (iv) above.

DETAILED DESCRIPTION OF THE INVENTION

Figure 1:
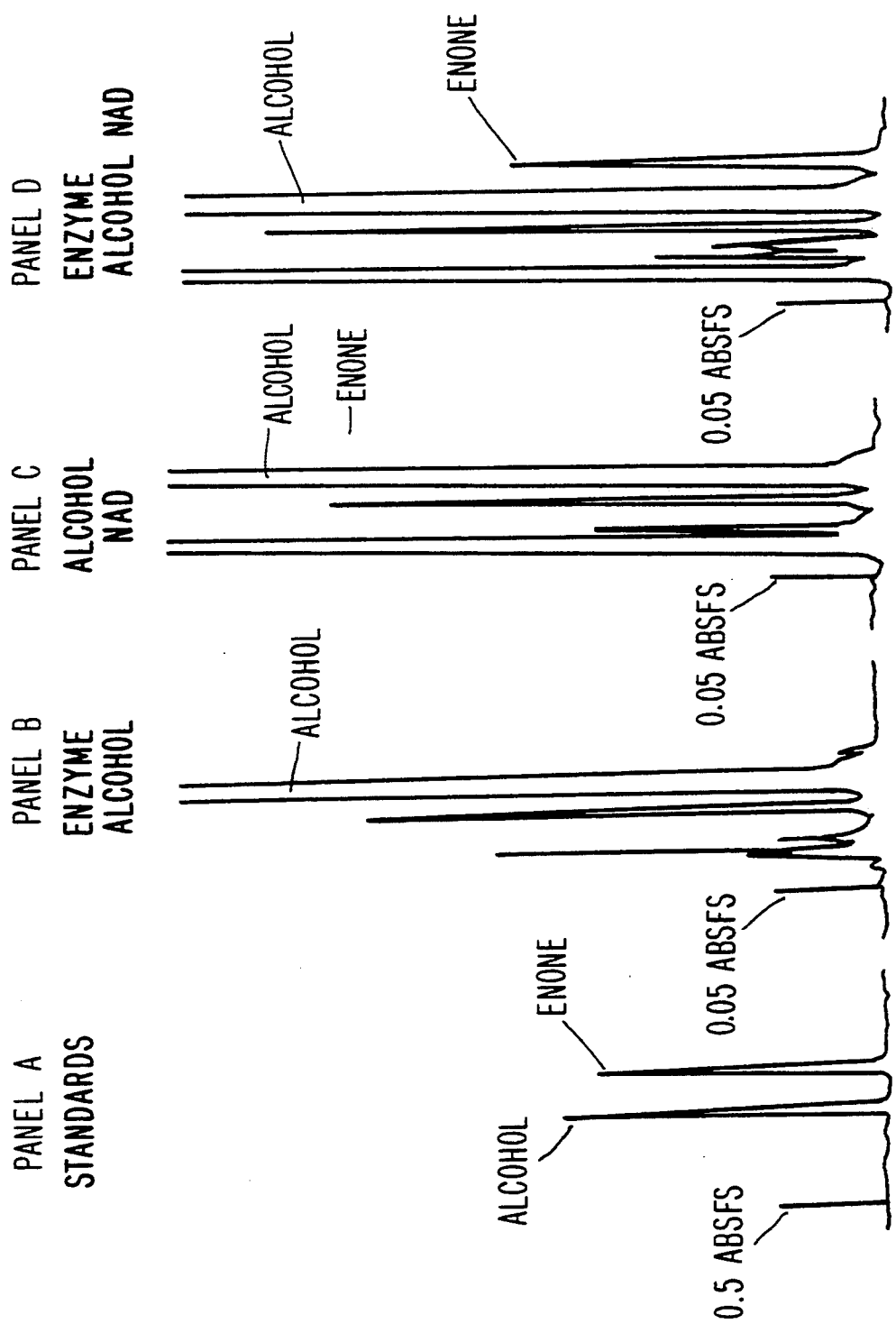
FIG. 1 is a HPLC chromatogram identifying the product of the enzyme catalyzed oxidation of 1-(4'-nitrophenyl)-2-propen-1-ol.

Studies show that the allylic alcohol 1-(4'-nitrophenyl)-2-propen-1-ol can be oxidized by 3α-HSD in the presence of NAD+ ($K_m$=2.02 mM and $V_{max}$=0.58 μmoles/min/mg), to yield the active Michael acceptor 1-(4'-nitrophenyl)-2-propen-1-one, which has been identified by HPLC (high performance liquid chromatography), as shown in FIG. 1.

Figure 2A:
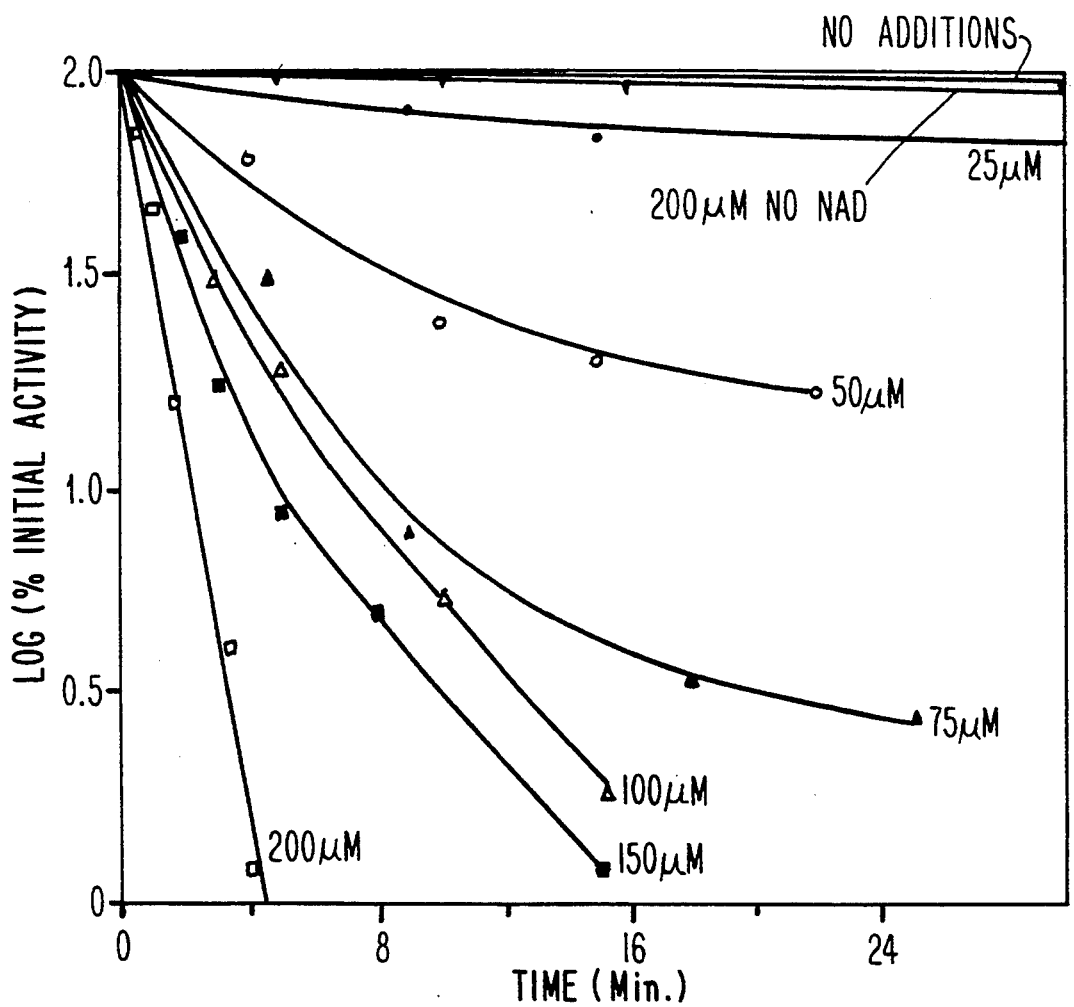
FIGS. 2a and 2b are plots showing the time dependent inactivation of 3α-HSD by 1-(4'-nitrophenyl)-2-propen-1-ol.
Figure 2B:
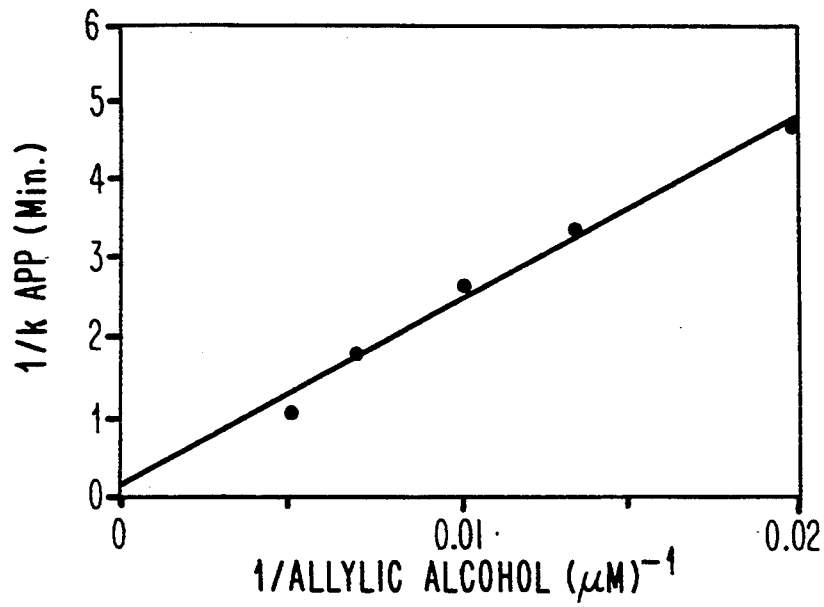

Enzymatic oxidation of the allylic alcohol (I) by 3α-HSD in the presence of micromolar concentrations of NAD+ results in a time-dependent loss of 3α-HSD activity, as seen in FIG. 2a. The presence of NAD+ is obligatory for the inactivation of 3α-HSD by the allylic alcohol. Analysis of this data by the method of Kitz and Wilson, [J. Biol. Chem., 1962, 237;10, 3245–3249], yields a $K_i$ of 1.2 mM for the alcohol and a $t_\frac{1}{2}$ life for the enzyme at a saturating allylic alcohol concentration of 8 seconds, as shown in FIG. 2b.

Figure 3A:
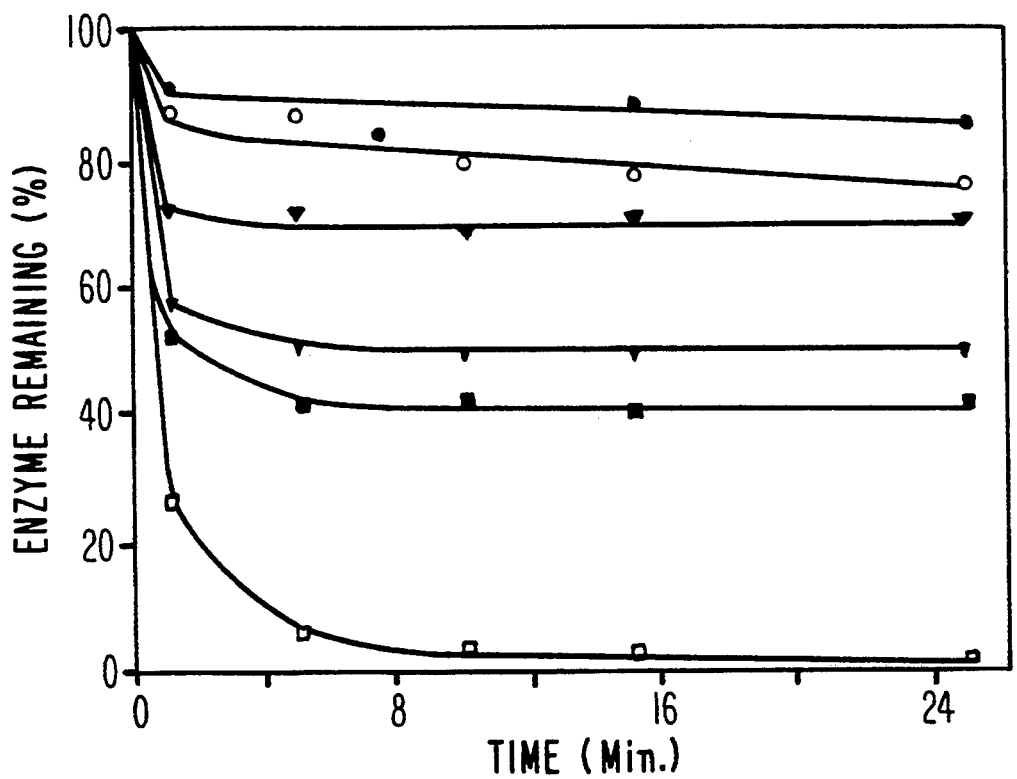
FIGS. 3a and 3b are plots showing the time dependent inactivation of 3α-HSD by 1-(4'-nitrophenyl)-2-propen-1-one.
Figure 3B:
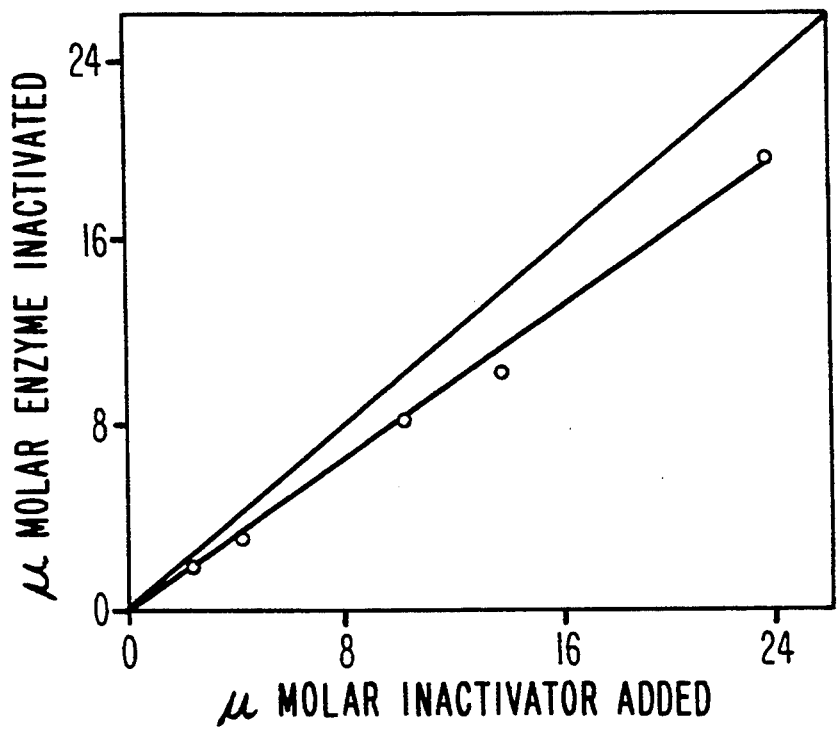

The enone (III), produces inactivation of 3α-HSD at a rate which is too fast to accurately measure under the conditions employed. Incubation of sub-stoichiometric quantities of enone (III), with purified 3α-HSD results in the titration of 3α-HSD activity, as shown in FIG. 3.

Comparison of the rate of allylic alcohol oxidation with that of enzyme inactivation suggests that 10 molecules or less of the allylic alcohol (I) are oxidized for every molecule of enzyme inactivated. This ratio, known as the partition ratio, is formally defined as $k_{cat}/k_{inact}$; for 1-(4'-nitrophenyl)-2-propen-1-ol it is estimated to be equal to 5.3, which is close to the theoretical limit of 1.

The acetylenic alcohol, 1-(4'-nitrophenyl)-2-propyn-1-ol (III), is oxidized by the enzyme with a $K_m$ and $V_{max}$ of 750 mM and 0.3 μMoles/min/mg, respectively, to yield the acetylenic ketone. Once formed, the acetylenic ketone (IV) is highly reactive. Evidence that the acetylenic ketone is the product of enzymatic oxidation was obtained by trapping the enzymatic oxidation product as stable monothioether adducts with 2-mercaptoethanol. The adducts trapped in the enzymatic reaction were then characterized by comparing their retention times to synthetic standards of monothioether adducts by HPLC. Like the enone (III), the acetylenic ketone (IV) inactivates 3α-HSD in a rapid and stoichiometric manner.

Irrespective of whether the allylic alcohol, acetylenic alcohol or their corresponding ketones are used to inactivate 3α-HSD, inactivation is accompanied by stable covalent bond formation between the enzyme and the inactivator. Thus, enzyme activity does not return upon either gel filtration or extensive dialysis of the inactivated enzyme.

Three types of experimental evidence indicate that both the enone (III) and the acetylenic ketone (IV) alkylate the pyridine nucleotide binding domain in preference to the steroid binding site of the enzyme. First, steady state kinetic measurements indicate that the enone (III) and the acetylenic ketone (IV) are competitive inhibitors of NAD+ binding and non-competitive or mixed inhibitors of androsterone binding. Second, NAD+ can provide complete protection of 3α-HSD from inactivation by (III) and (IV), whereas androsterone and other compounds which are competitive for the steroid binding site slow the rate of inactivation but do not completely block this event. Third, chromatographic experiments using the immobilized nucleotide analog Cibacron Blue indicate that both native enzyme and enzyme inactivated with the steroid affinity alkylator, 17β-bromoacetoxy-5α-androstan-17β-ol-3-one, bind tightly to the immobilized nucleotide analog. By contrast, enzyme inactivated by either (III) or (IV) has no affinity for the immobilized nucleotide analogue. This experimental evidence implies that the alkylators (III) and (IV) covalently modify the nucleotide binding domain of 3α-HSD.

Although a number of HSD's oxido-reduce a variety of non-steroidal substrates, the non-steroidal suicide substrates covered by this invention appear to be highly selective agents for 3α-HSD. A broad screen was conducted in which the allylic (I) and acetylenic alcohols (II) were examined as suicide substrates of the following enzymes: 3α-HSD and 3(17)β-HSD (*Pseudomonas testosteroni*), 3α,20α-HSD (*Streptomyces hydrogenase*), 20α-HSD (rat ovary), 3β-HSD (rat liver), alcohol dehydrogenase (yeast), lactate dehydrogenase (porcine heart) and 3α-HSD (rat liver). The results indicated that only rat liver 3α-HSD effectively oxidized the alcohols and was subsequently inactivated by the enzyme generated ketones.

Studies indicate that the vinyl ketone 1-(4'-nitrophenyl)-2-propen-1-one (iii) and the acetylenic ketone 1-(4'-nitrophenyl)-2-propyn-1-one (iv) cause time and concentration dependent inactivation of a semi-purified preparation of cyclooxygenase obtained from sheep seminal vesicle microsomes. For compound (iii), the concentration required to inactivate 50% of the enzyme activity was 837 μM and the $t_\frac{1}{2}$ life at saturation was 1–2 minutes. By contrast, acetyl salicylate at a concentration of 100 μM inactivated 50% of this semi-purified preparation of cyclooxygenase over 20 hours, as shown in FIGS. 4(a–c).

Preparation of the Compounds

Latent Michael acceptors of the general formula (iii) may be synthesized directly from the corresponding benzaldehyde and vinyl or acetylene magnesium bromide, as shown in Scheme 3. Subsequent oxidation yields the active Michael acceptor of general formula (i).

Scheme 3

The synthesis of N-phenyl-anthranilic acid analogues incorporating the latent aromatic Michael acceptors described above may be undertaken by a number of routes. The two principal reactions used to synthesize

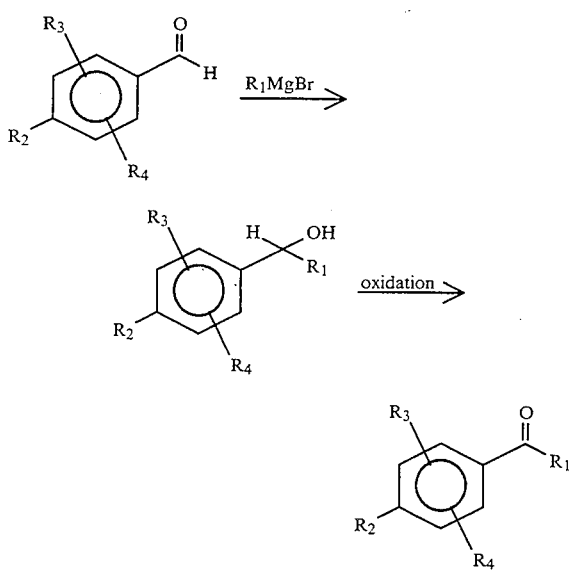

N-phenyl-anthranilic acids are the Ullmann reaction (for thorough reviews: Acheson, "Acridines" in The Chemistry of the Heterocyclic Compounds (Interscience, New York, 1956); Albert, "The Acridines" (Edward-Arnold Co. London, 1951) and diphenyliodonium-2-carboxylate (DPIC) coupling [J. Org. Chem., 1980, 45;11, 2127–2131], both are shown schematically below. Because they are largely complimentary in the substitutions they allow, diverse functionalities can be incorporated into the N-phenyl-anthranilic acid nucleus, as in Scheme 4.

Scheme 4

The 1-methyl-pyrrole acetic acid and arylpropionic acid analogs may be prepared by analogous methods known in the art.

The preparation of the compounds of this invention will be further illustrated by the following examples.

Example 1

Preparation of 1-(4'-nitrophenyl)-2-propen-1-ol, (I) and 1-(4'-nitrophenyl)-2-propen-1-one, (II).

p-Nitrobenzaldehyde (1 g, 6.6 mMoles) and 30 ml of dry tetrahydrofuran (THF) was stirred at 0° C. in a septum sealed flask equipped with a pressure equalizing funnel. After purging with dry nitrogen, 7 ml of 1M vinyl magnesium bromide in THF was added dropwise under a nitrogen atmosphere. After addition of the Grignard reagent, the reaction was allowed to stir at room temperature for 30 min. The bulk of the THF was removed under vacuum and the reaction was quenched by pouring it into a slurry containing 200 ml of water, crushed ice and 100 ml of ether. The final pH of the slurry was adjusted to near neutral by dropwise addition of 2M sulfuric acid. The product was extracted with ether and the pooled extracts were washed twice with 30 ml of water and twice with 30 ml of saturated NaCl. Ether was removed under vacuum yielding a dense yellow oil which was chromatographed on preparative silica TLC plates using toluene:acetonitrile 10:1 (v/v) as running solvent. Elution of the product from silica with methanol yielded 700 mg of semi-crystalline 1-(4'-nitrophenyl)-2-propen-1-ol. Recrystallization from toluene and then ethanol gave needles of pure product. IR: (chloroform) (cm$^{-1}$) —OH, 3600, 1040; intermolecular —OH, —C=CH$_2$, 3020, 2870, 985, 935 aromatic, 1607, 858; —NO$_2$, 1510, 1350, 872. NMR: δ (p.p.m.) ([$^2$H]chloroform), 2.2 (1H, broad s, —OH, D$_2$O exchangeable), 5.26 (1H, d, J$_{2,3}$cis 10.6 Hz, J$_{3,3}$gem 1 Hz, —C=CH$_2$), 5.32 (1H, broad m, —CH=C), 5.42 (1H, d, J$_{2,3}$trans 17.2 Hz, J$_{3,3}$gem 1 Hz —C=CH$_2$), 6.0

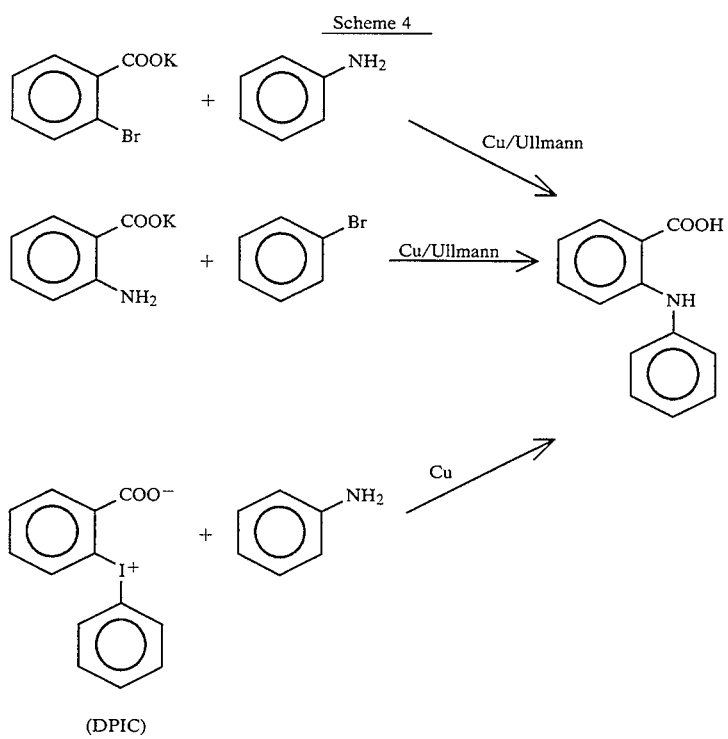

(DPIC)

(1H, m, C—CH═C), 7.4 (2H, d, J 9 Hz, aromatic), 8.21 (2H, d, J 9 Hz, aromatic). $UV_{max}$ 272 nm, $\epsilon = 10,500 M^{-1} cm^{-1}$; Mp.=55° C.

Oxidation of 1-(4'-nitrophenyl)-2-propen-1-ol (200 mg) to yield 1-(4'-nitrophenyl)-2-propen-1-one was conducted in 5 ml of acetone at room temperature by the dropwise addition of Jones reagent, ($CrO_3/H_2SO_4$) with stirring. Addition of the reagent was continued until the reaction remained yellow for more than 5 min. Addition of 0.2 ml of methanol consumed the excess oxidant. The reaction was poured into 40 ml of water and neutralized with 1M NaOH. The product was extracted into toluene until completion and the pooled extracts were washed with saturated $Na_2CO_3$ followed by saturated NaCl. Removal of the toluene under vacuum gave a semi-crystalline mass of 1-(4'-nitrophenyl)-2-propen-1-one. Recrystallization from toluene then ethanol gave pure needles of product. IR: (chloroform) ($cm^{-1}$) C═O, 1670; C═$CH_2$, 1002, 911; aromatic, 1610, 855; —$NO_2$, 1520, 1350, 870. NMR: δ (p.p.m.) ([$^2H$]chloroform) 6.15 (1H, m), 6.6 (1H, m), 7.2 (1H, m), 8.1 (2H, d, J 8 Hz, aromatic), 8.3 (2H, d, J 8 Hz, aromatic); $UV_{max}$ 266 nm, $\epsilon_{266}=17,700 M^{-1} cm^{-1}$; MP=89°–90° C.

Example 2

Preparation of 1-(4'-nitrophenyl)-2-propyn-1-ol, (II) and 1-(4'-nitrophenyl)-2-propyn-1-one, (IV).

Synthesis of the acetylenic alcohol (II), and ketone, (IV), can be accomplished by the general method outlined for the allylic alcohol (I), and the enone (II), by substituting acetylene magnesium bromide for vinyl magnesium bromide. Acetylenic alcohol (II) IR: (chloroform) ($cm^{-1}$) —OH, 3590, 1040; intermolecular —OH, 3550-3350; —C≡CH, 3300, 2125; aromatic 1590, 844; $NO_2$, 1500, 1340, 852; $UV_{max}$=269 nm in acetonitrile, $\epsilon_{259}=6,600 M^{-1} cm^{-1}$. NMR: δ (p.p.m.) ([$^2H$] chloroform) 2.75 (1H, d, J 2 Hz, —CH—C≡C—), 3.0 (1H, broad s, $D_2O$ exchangeable, —COH—C≡C), 5.6 (1H, d, J 2 Hz, —C≡CH), 7.6 (2H, d, J 9 Hz, aromatic), 8.2 (2H, d, J 9 Hz, aromatic). MP=57° C.

Acetylenic ketone (III): IR: (chloroform) ($cm^{-1}$) C═O, 1660; —C≡CH, 3300, 2100; aromatic, 1605, 855; $NO_2$, 1520, 1340, 870. $UV_{max}$=271 nm in acetonitrile, $\epsilon_{271}=16,620 M^{-1} cm^{-1}$. NMR: δ (p.p.m.) ([$^2H$] chloroform) 3.58 (1H, s, —C≡CH), 8.37 (4H, s, aromatic). MP=125°–127° C.

Example 3

Preparation of 2'-nitro-5'-(2-propen-1-ol)-anthranilic acid (V).

(a) As shown in Scheme 5, oxidation of 3-fluoro-4-nitrotoluene by one of two routes affords the corresponding aldehyde. Then, as in Example 1, addition of vinyl magnesium bromide will yield the corresponding allylic alcohol. Subsequent coupling with 2-amino-benzoic acid via an Ullmann reaction will yield the N-phenyl-anthranilic acid containing a latent Michael acceptor.

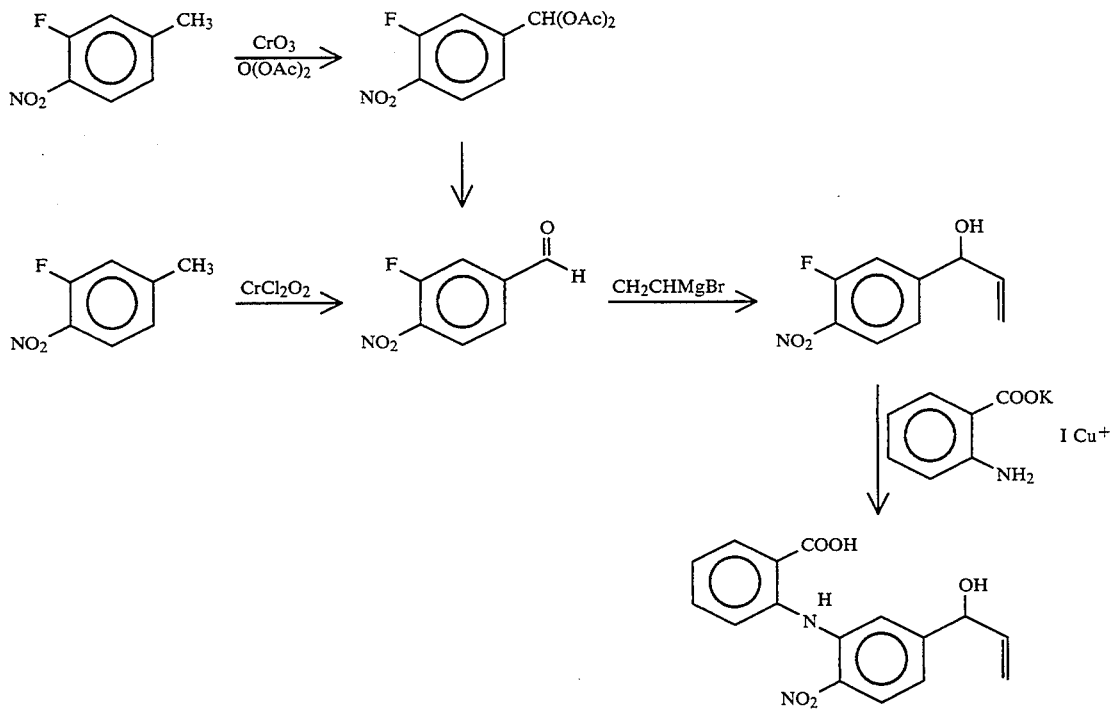

Scheme 5

Synthesis of the active Michael acceptor, the last step above, can be accomplished by a number of mild oxidants including those described by D. Swern, Synthesis, 1981, 139, 165–185, (1981), $MnO_2$ [Synthesis, 1976, 133, 65–76], or chromic anhydride in hexamethyl phosphoric triamide which is specific for allylic alcohols [Synthesis, 1976, 133, 394–398].

(b) As shown in Scheme 6, oxidation of 3-bromo-4-nitrotoluene affords the corresponding aldehyde. Addition of vinyl magnesium bromide yields the corresponding allylic alcohol. Subsequent coupling with 2-amino-benzoic acid via an Ullmann reaction provides the N-phenyl-anthranilic acid containing a latent Michael acceptor.

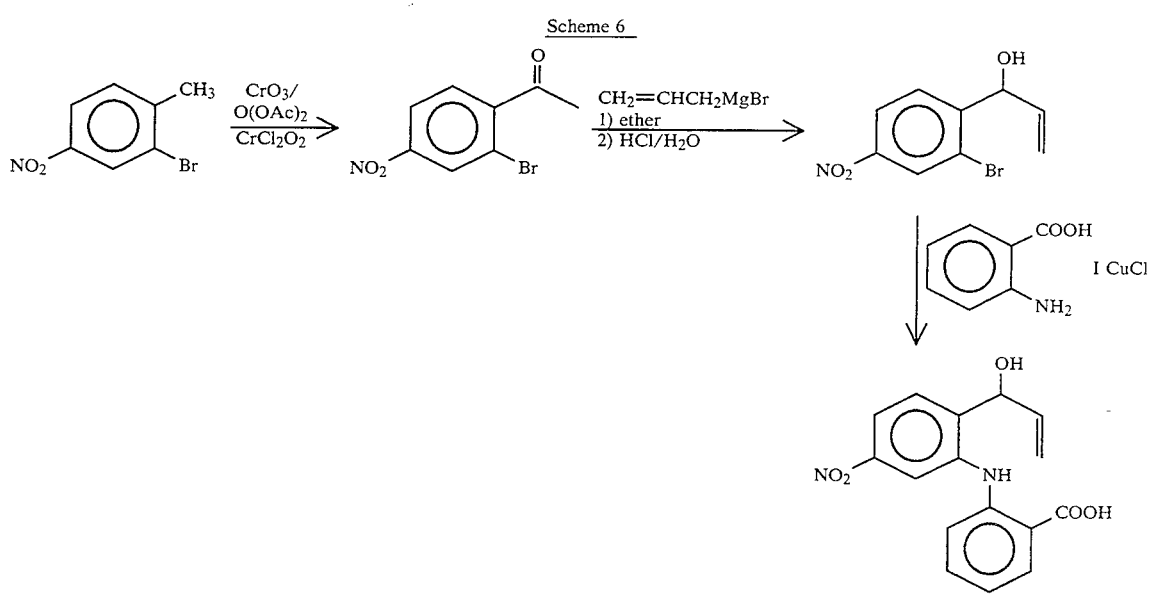

(c) As shown in Scheme 7, coupling of 3-bromo-4-nitrotoluene with 2-amino-benzoic acid via an Ullmann reaction yields an N-phenyl-anthranilic acid. After protection of the acid with 2-amino-2-methyl-1-propanol, oxidation affords the corresponding aldehyde. Addition of vinyl magnesium bromide and deprotection provides the N-phenyl-anthranilic acid containing a latent Michael acceptor.

Figure legends

FIG. 1 shows the identification of the enzyme catalyzed oxidation product of the allylic alcohol (I) by HPLC. Systems (1 ml) containing 1.43 μg of enzyme, 2.3 mM NAD+ and 1.3 mM allylic alcohol in 0.1M potassium phosphate buffer pH 7.0 with 4% acetonitrile as a co-solvent were incubated at 25° C. until no further change in the absorbance at 340 nm was observed. Por-

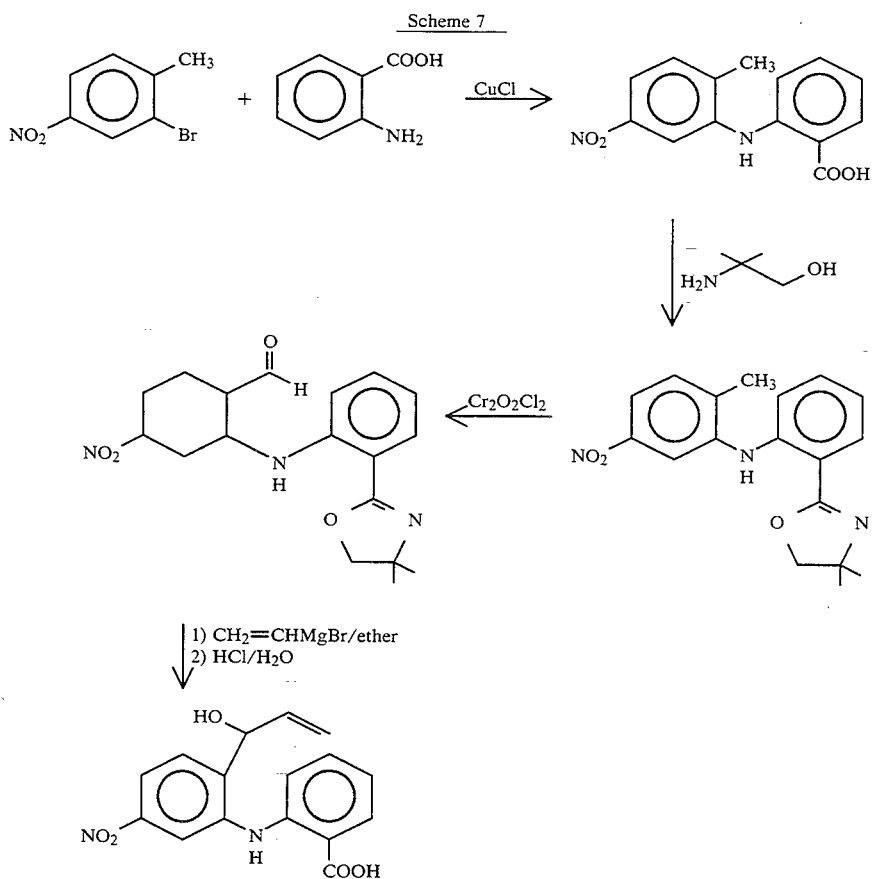

tions of the reaction mixture were chromatographed on a Waters C18 Bondapak column pre-calibrated with standards using 45% acetonitrile in water as the mobile phase. Retention times for the allylic alcohol (I) and enone (III) standards (panel a); chromatogram resulting from the incubation containing 1.43 μg of enzyme and 1.3 mM allylic alcohol, omitting NAD+ (panel b); chromatogram resulting from the incubation containing 2.3 mM NAD+ and 1.3 mM allylic alcohol, omitting enzyme (panel c); chromatogram resulting from the incubation containing the complete system, 1.43 μg of enzyme, 2.3 mM NAD+ and 1.3 mM allylic alcohol (panel d).

FIG. 2 shows the time dependent inactivation of 3α-HSD by the concentrations of allylic alcohol (I) indicated, in the presence and absence of NAD+. 3α-HSD (24 μM of purified enzyme) was incubated in systems (30 μl) containing 1.2 mM NAD+, 10 mM potassium phosphate buffer pH 7.0, 1 mM EDTA and 5% acetonitrile as a co-solvent. Enzyme activity was followed over time by diluting an aliquot of the incubation mixture into a 1 ml assay containing: 2.3 mM NAD+ and 75 μM androsterone in 0.1M potassium phosphate buffer pH 7.0, with 4% acetonitrile as a co-solvent. Initial rates were determined spectrophotometrically by measuring the rate of NADH formation at 340 nm. Because of the 100 fold or greater dilution of the enzyme into the assay, the initial rate measured is an indication of the enzyme activity remaining at that time. Semi-log plots of the amount of enzyme remaining vs. time are curvilinear (panel a). Initial rates of inactivation ($k_{app}$'s) were estimated by taking tangents to these curves. Data was replotted as $1/k_{app}$ vs $1/$allylic alcohol from which $k_{inact}$ (the rate constant for enzyme inactivation) and $K_i$ (the binding constant of the allylic alcohol) were determined, (panel b).

FIG. 3 shows time dependent inactivation of 3α-HSD by the enone (III). Inactivation of 3α-HSD (24 μM) was conducted in incubations (60 μl) of 10 mM potassium phosphate buffer pH 7.0 containing 1 mM EDTA and 4% acetonitrile as a co-solvent. After the initial enzyme activity was determined (see the legend of FIG. 2 for assay composition), the concentration of inactivator indicated (●=0 μM, o=2.1 μM, ▼ =4.9 μM, ▽=10.0 μM, ■ =15.0 μM, []24.0 μM) was added and the sample incubated at 25° C. Over time, samples were withdrawn and diluted into the standard assay to determine the amount of enzyme activity remaining. A secondary plot of the amount of enzyme inactivated vs. the amount of inhibitor added provided the stoichiometry of inactivation when corrected for nonspecific loss of enzyme activity (panel b). The continuous line without points is a theoretical line for a stoichiometry of 1:1.

Figure 4A:
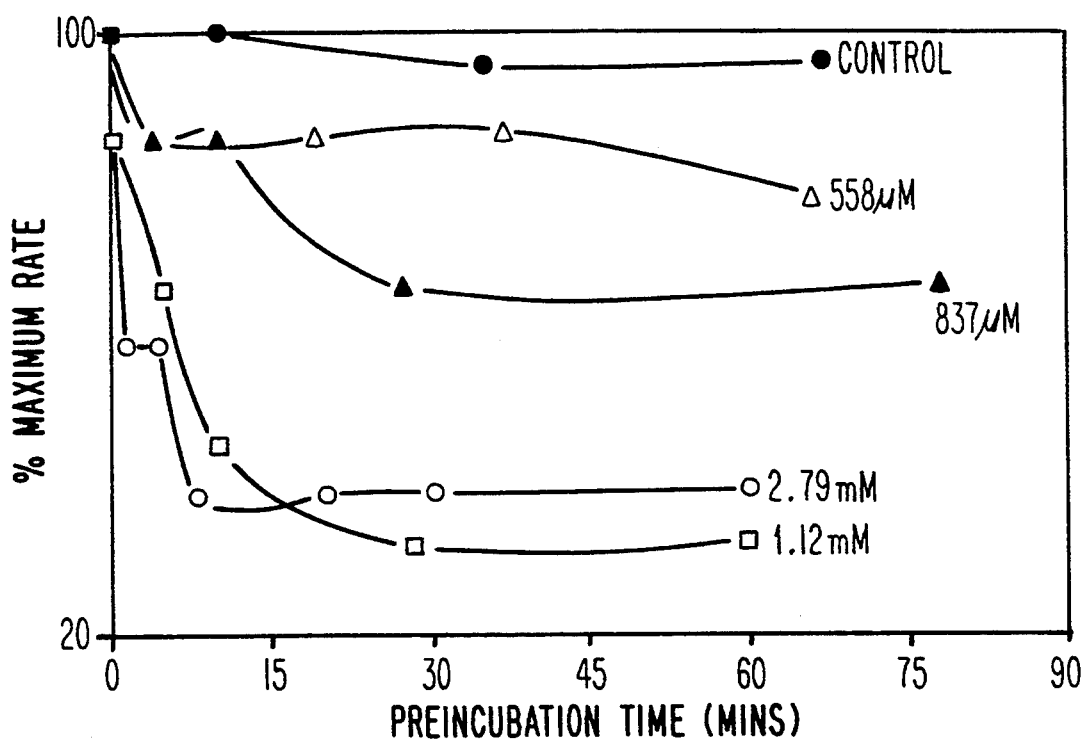
FIGS. 4a, 4b, and 4c are plots showing the time dependent inactivation of cyclooxygenase by 1-(4'-nitrophenyl)-2-propen-1-one, by 1-(4'-nitrophenyl)-2-propyn-1-one, and aspirin, respectively.
Figure 4B:
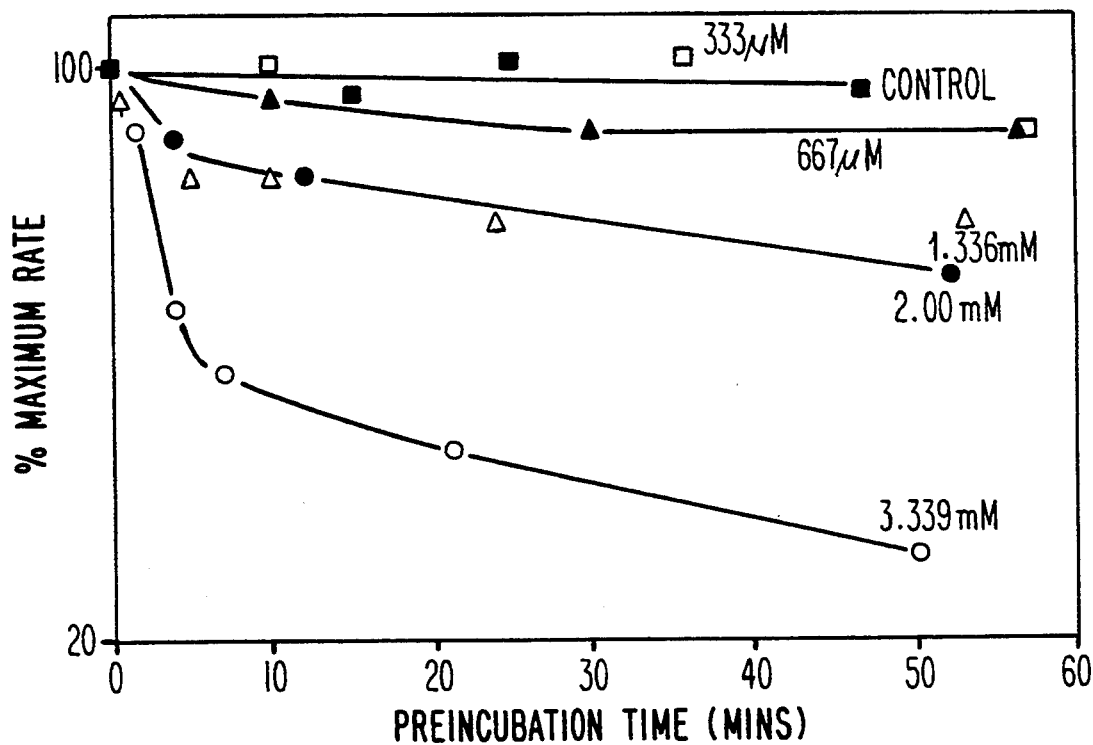
Figure 4C:
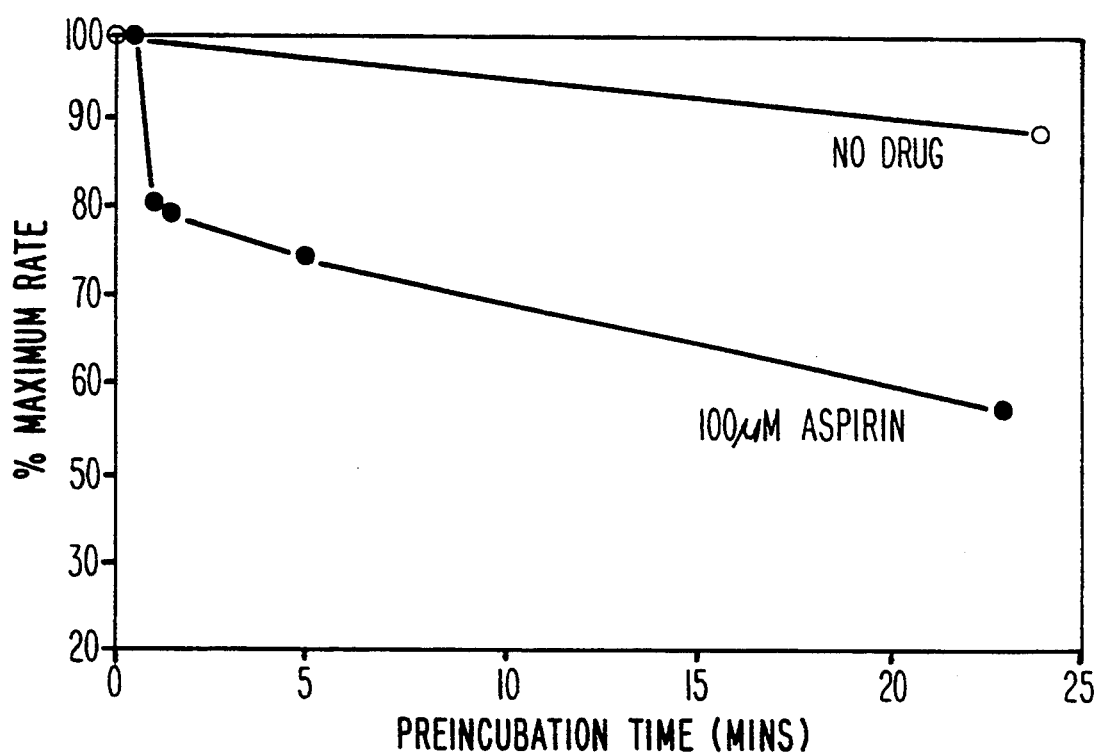

FIG. 4 shows the time dependent inactivation of cyclooxygenase by the vinyl ketone 1-(4'-nitrophenyl)-2-propen-1-one (FIG. 4a), the acetylenic ketone 1-(4'-nitrophenyl)-2-propyn-1-one (FIG. 4b), and aspirin (FIG. 4c). Semi-purified cyclooxygenase (480 μg) was pre-incubated in 100 μl systems containing the inhibitor concentrations indicated, along with 50 mM Tris-HCl (pH=7.2), 100 μM EDTA, 1 mM phenol, 1 μM hematin, 1% Tween, and 10% DMSO. At the time intervals shown, 5 μl aliquots were removed and diluted into a 600 μl assay system containing 100 mM potassium phosphate (pH=7.2), 1 mM phenol, and 100 μM arachidonic acid. The rate of oxygen consumption was then measured. The maximum rate of oxygen uptake observed in these assays was 1.875 μmoles of oxygen consumed per minute per milligram protein.

The data presented herein suggest that compounds of formulas (i), (ii), (iii) and (iv) could be used in pharmaceutical compositions useful as adjuvants in androgen therapy and as anti-inflammatory drugs. This invention, therefore, further relates to pharmaceutical compositions comprising one or more compounds of formulas (i), (ii), (iii) and (iv), or pharmaceutically acceptable salts thereof in combination with any of the conventional pharmaceutically acceptable carriers or diluents. Suitable pharmaceutical carriers are well known in the art and are described, for example, in Remington's Pharmaceutical Sciences, E. W. Martin, a standard reference text in this field. Pharmaceutically acceptable salts include, but are not limited to, salts of hydrochloric, hydrobromic, sulfuric, benzenesulphonic, acetic, fumaric, oxalic, malic and citric acids, as well as hydroxides of potassium and sodium.

What is claimed is:

1. A pharmaceutical composition comprising a compound of the formula:

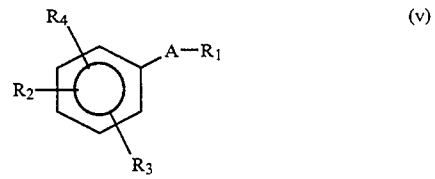

(v)

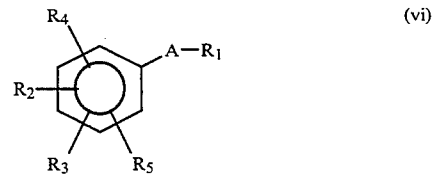

(vi)

where

A is —C(O)— or —CH(OH)—;

$R_1$ is selected from the groups consisting of CH=CH$_2$, CH=CH—OMe, CH=CH—OEt, C≡CH, C≡C—OMe, and C≡C—OEt;

$R_2$ is selected from the groups consisting of NO$_2$, Z, CH$_2$Z, CHZ$_2$, CZ$_3$, COOH, NH$_2$ and OH;

$R_3$ and $R_4$ are independently selected from the groups consisting of H, NO$_2$, Z, CH$_2$Z, CHZ$_2$, CZ$_3$, COOH, NH$_2$ and OH;

$R_5$ is selected from the groups consisting of:

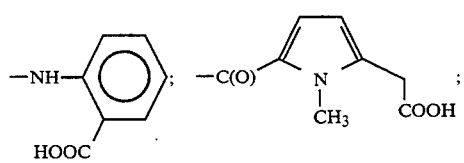

and

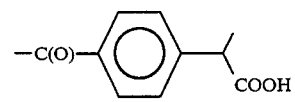

and Z is a halogen atom, or its pharmaceutically acceptable salt, provided that, for compounds of formula (v), when $R_2$=NO$_2$ and $R_3$ and $R_4$=H, then A=—CH(OH)— and $R_1$ is other than C≡CH.

2. The pharmaceutical composition of claim 1 where A is —C(O)—.

3. The pharmaceutical composition of claim 1 where A is —CH(OH)—.

4. The pharmaceutical composition of claim 1 where $R_1$ is CH=CH$_2$.

5. The pharmaceutical composition of claim 1 where $R_1$ is C≡CH.

6. The pharmaceutical composition of claim 1 where $R_2$ is NO$_2$.

7. The pharmaceutical composition of claim 1 where $R_3$ and $R_4$ are H.

8. The pharmaceutical composition of claim 1 where said compound is 1-(4'-nitrophenyl)-2-propen-1-ol.

9. The pharmaceutical composition of claim 1 where said compound is 1-(4'-nitrophenyl)-2-propyn-1-ol.

10. A compound of the formula:

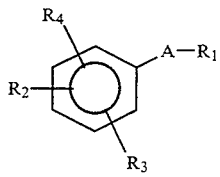

(v)

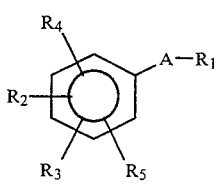

(vi)

where

A is —C(O)— or —CH(OH)—;

$R_1$ is selected from the groups consisting of CH=CH$_2$, CH=CH—OMe, CH=CH—OEt, C≡CH, C≡C—OMe, and C≡C—OEt;

$R_2$ is selected from the groups consisting of NO$_2$, Z, CH$_2$Z, CHZ$_2$, CZ$_3$, COOH, NH$_2$ and OH;

$R_3$ and $R_4$ are independently selected from the groups consisting of H, NO$_2$, Z, CH$_2$Z, CHZ$_2$, CZ$_3$, COOH, NH$_2$ and OH;

$R_5$ is selected from the groups consisting of:

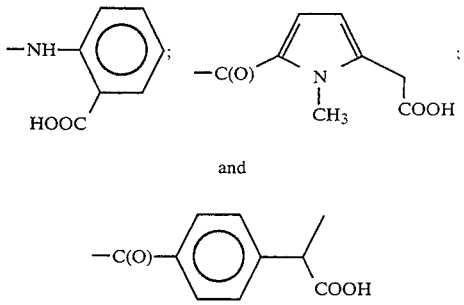

and and Z is a halogen atom, provided that, for compounds of formula (v), when $R_2$=NO$_2$ and $R_3$ and $R_4$=H, then A=—CH(OH)— and $R_1$ is other than C≡CH.

11. A compound of claim 10 where A is —C(O)—.

12. A compound of claim 10 where A is —CH(OH)—.

13. The method of claim 10 where $R_1$ is CH=CH$_2$.

14. The method of claim 10 where $R_1$ is C≡CH.

15. The method of claim 10 where $R_2$ is NO$_2$.

16. The method of claim 10 where $R_3$ and $R_4$ are H.

17. The method of claim 10 where said compound is 1-(4'-nitrophenyl)-2-propen-1-ol.

18. The method of claim 10 where said compound is 1-(4'-nitrophenyl)-2-propyn-1-ol.

* * * * *